(12) United States Patent
Cerda et al.

(10) Patent No.: US 8,791,246 B2
(45) Date of Patent: *Jul. 29, 2014

(54) ENZYMATIC SUBSTRATES FOR MULTIPLE DETECTION SYSTEMS

(75) Inventors: Blas Cerda, Milford, MA (US); Mark Norman Bobrow, Lexington, MA (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/438,029

(22) Filed: Apr. 3, 2012

(65) Prior Publication Data

US 2012/0190043 A1    Jul. 26, 2012

Related U.S. Application Data

(62) Division of application No. 12/403,790, filed on Mar. 13, 2009.

(60) Provisional application No. 61/036,211, filed on Mar. 13, 2008.

(51) Int. Cl.
| | |
|---|---|
| *C07C 237/22* | (2006.01) |
| *C07K 5/06* | (2006.01) |
| *C07K 5/068* | (2006.01) |
| *C12Q 1/34* | (2006.01) |
| *C07H 15/203* | (2006.01) |
| *C07K 19/00* | (2006.01) |

(52) U.S. Cl.
CPC ... *C12Q 1/34* (2013.01); *C07K 5/06* (2013.01); *G01N 2333/924* (2013.01); *G01N 2458/15* (2013.01); *C07H 15/203* (2013.01); *C07C 237/22* (2013.01); *C07K 19/00* (2013.01)
USPC ........... 536/17.4; 560/251; 564/157; 564/159

(58) Field of Classification Search
None
See application file for complete search history.

(56) References Cited

U.S. PATENT DOCUMENTS

| 4,968,785 | A | 11/1990 | Moser et al. | |
|---|---|---|---|---|
| 6,852,544 | B2 | 2/2005 | Aebersold et al. | |
| 8,268,865 | B2 * | 9/2012 | Glinka et al. ................. | 514/311 |
| 2005/0232929 | A1 | 10/2005 | Kadkhodayan et al. | |

FOREIGN PATENT DOCUMENTS

| EP | 0631779 A1 | 1/1995 |
|---|---|---|
| JP | 11116589 A | 4/1999 |
| JP | 2006524040 A | 10/2006 |
| JP | 2007532882 A | 11/2007 |
| JP | 4364197 B2 | 11/2009 |
| WO | WO-0011208 A1 | 3/2000 |
| WO | 00/61543 A2 | 10/2000 |
| WO | 2004072238 A2 | 8/2004 |
| WO | 2007013601 A1 | 2/2007 |
| WO | WO-2007/106816 A2 | 9/2007 |

OTHER PUBLICATIONS

Halling et al.; Understanding Enzyme Action on Immobilised Substrates; vol. 16, No. 4,; Aug. 1, 2005; pp. 385-392.
Gelman, Benjamin B., et al.; Mononuclear Phagocyte Hdrolytic Enzyme Activity Associated with Cerebral HIV-1 Infection; American Journal of Pathology, vol. 151, No. 5, Nov. 1997; pp. 1437-1446.
Demartino, George N. et al.; Thyroid hormones control lysosomal enzyme activities in liver and skeletal muscle; Proc. Natl. Acad. Sci. USA, vol. 75, No. 3; pp. 1369-1373; Mar. 1978; Cell Biology.
Boot, Rolf G. et al.; Identification of the Non-lysosomal Glucosylceramidase as B-Glucosidase 2; Journal of Biological Chemistry; Jan. 12, 2007; vol. 282, No. 2; pp. 1305-1312.
Alexa Fluor Succinimidyl Esters; Invitrogen; Molecular Probes, Revised: Feb. 6, 2007, pp. 1-5.
Amine-Reactive Probes; Invitrogen, Molecular Probes; Revised: Feb. 6, 2007; pp. 1-9.
Amplex® Red Galactose/Galactose Oxidase Kit (A22179), Molecular Probes Production Information, Amplex® Red Galactose/Galactose Oxidase Kit, Revised: Oct. 1, 2004, pp. 1-4.
Amplex® Red Glucose/Glocose Oxidase Assay Kit; Invitrogen Molecular Probes, Revised: May 22, 2006; pp. 1-7.
Leonard, Renaud et al.; The *Drosophila* fused lobes Gene Encodes an N-Acetylglucosaminidase involved in N-Glycan Processing; The Journal of Biological Chemistry; vol. 281, No. 8; pp. 4867-4875.
Lundquist, Ingmar et al.; Islet Acid Glucan-1, 4-x-Glucosidease: A Putative Key Enzyme in Nutrient-Stimulated Insulin Secretion; Endocrinology, vol. 137; No. 4; pp. 1219-1225.

(Continued)

*Primary Examiner* — Eric Olson
(74) *Attorney, Agent, or Firm* — Gifford, Krass, Sprinkle, Anderson & Citkowski, P.C.

(57) ABSTRACT

An inventive substrate is provided which includes a substrate compound of formula $A-B^1-B^2-B^3-B^4$: wherein A is a sugar moiety; $B^1$ is a linker moiety allowing the conjugation of moiety A and the remaining structure of the substrate; $B^2$ is a linker moiety with a free reactive amino group so as to be available for reaction with carboxylic acids or detectable tags; $B^3$ contains a permanently charged element such as a quaternary ammonium group so as to increase sensitivity for mass spectrometry analysis; and $B^4$ of various carbon length conferring specificity amongst individual substrates in detection methods. Also provided is a molecule of the formula $B^1-B^2-B^3-B^4$, with similar structural characteristics to an enzymatic product produced by the action of a target enzyme on an inventive substrate. Further provided are methods for using inventive substrates for detecting enzymatic activity.

12 Claims, 6 Drawing Sheets

(56) References Cited

OTHER PUBLICATIONS

Ramsay, Steven L. et al.; Determination of oligosaccharides and glycolipids in amniotic fluid by electrospray ionization tandem mass spectrometry; in utero indicators of lysosomal storage diseases; Molecular Genetics and Metabolism 83 (2004) pp. 231-238; www.elsevier.com <http://www.elsevier.com>.

Immunosurveillance of Algucerase Enzyme Therapy for Gaucher Patients; Induction of Humoral Tolerance in Seroconverted Patients After Repeat Administration; Phagocytes Blood; vol. 93; No. 6; (Mar. 15); 1999; pp. 2081-2088.

Zhou, Mingjie et al; Two Fluorometric Approaches to the Measurement of Dextranase Activity; Analytical Biochemistry 260, 257-259; (1998); Article No. AB982733.

Li, Y et al.; Direct Multiplex Assay of Lysosomal Enzymes in Dried Blood Spots for Newborn Screening; Clinical Chemistry; vol. 50; pp. 1785-1796 (2004).

ELISA—Introduction to Antibodies; Introduction to Antibodies—Enzyme-Linked Immunosorbent Assay (ELISA); <http://www.chemicon.com>; pp. 1-6 (reprinted from website Jun. 1, 2007).

Gibbs, J. Immobilization Principles—Selecting the Surface; ELISA Technical Bulletin—No. 1; Corning Life Sciences, pp. 1-8 (2007).

Corning Assay Surfaces Selection Guide; <http://www.corning.com>; pp. 1-3 (Jul. 2001).

Cartine and Acylcarntines; Carntine and acylcarntines: structure, occurrence, biology and analysis, www.lipidlibrary.co.uk <http://www.lipidlibrary.co.uk>; pp. 1-2 (2007).

Cerezyme; pp. 1-2 (Dec. 3, 2007).

Biovision; Glucose Assay Kit; BioVision Research Products, pp. 1 of 1 (Apr. 2006).

Minimum Recommendations for Monitoring Patients with Non-Neuronopathic (Type 1) Gaucher Disease; Gaucher Registry; www.gaucherregistry.com; p. 1 of 1 (Mar. 2003).

\* cited by examiner

ENZYMATIC SUBSTRATES FOR MULTIPLE DETECTION SYSTEMS

CROSS-REFERENCE TO RELATED APPLICATIONS

This application is a Divisional, which depends from and claims priority to U.S. patent application Ser. No. 12/403,790, filed Mar. 13, 2009, which claims priority of U.S. Provisional Patent Application Ser. No. 61/036,211 filed Mar. 13, 2008, the contents of each of which are incorporated herein by reference.

FIELD OF THE INVENTION

The present invention relates to analytical reagents for detecting enzymatic activity using detection methods such as mass spectrometry, immunoassay, and high performance liquid chromatography. In one aspect, the present invention relates to substrates for detecting lysosomal enzyme activity.

BACKGROUND OF THE INVENTION

Lysosomal storage disorders are a group of inherited disorders characterized by deficiencies in specific enzymes in the body, which results in the body's inability to break down metabolic substances. As an example, Fabry disease is a lysosomal storage disorder seen in one out of every 40,000 people. It is caused by a deficiency in the enzyme alpha-galactosidase which results in the body's inability to break down specific fatty substances called globotriaosylceramides. A second example is Gaucher disease, a lysosomal storage disorder caused by an inability to break down fatty substances or lipids called glucosylceramides (also called glucocerebrosides). Individuals with Gaucher disease do not make glucocerebrosidase, an enzyme needed to break down these fatty substances. These fatty substances then accumulate in cells of the liver, spleen, and bone marrow. A third example is Pompe disease, a lysosomal storage disorder caused by a deficiency in the enzyme acid alpha-glucosidase, which is needed to break down certain sugars called glycogen. When the enzyme acid alpha-glucosidase is missing, glycogen accumulates in various tissues and organs in the body.

Lysosomal storage disorders are, for the most part, childhood disorders although some manifest in adulthood. In most of them, patients are normal at birth and have progressive neurological deterioration beginning at some later time. The clinical phenotype depends on the type and severity of the biochemical defect. Some of these lysosomal disorders, such as Pompe disease and Krabbe disease, manifest primarily in infancy. There have been ongoing efforts in developing methods to detect such disorders before the onset of clinical symptoms so that therapeutic interventions can be initiated.

Over the past decade laboratories that test for metabolic disorders have introduced tandem mass spectrometry into their newborn screening programs. Tandem mass spectrometry continues to gain popularity in the clinic because this technology allows for assay of many metabolites in a single sample. For example, this technology has been implemented as a routine clinical practice for the detection of hereditary metabolic disorders in newborns using dry blood spot samples (Schulze A et al., *Pediatrics* 2003; 111:1399-406). Although lysosomal enzyme activities can be quantified using tandem mass spectrometry (Gelb M H et al., *Clinical Chemistry* 50:10, 1785-1796, 2004), published assay methods have not been readily adaptable to a clinical setting due to cumbersome procedures and harsh assay components such as chloroform.

A second commonly used clinical assay protocol is the enzyme linked immunosorbent assay (ELISA). Several biomarkers are presently used to detect and monitor Gaucher disease (see, for example Aerts, J M, and Hollack, C D, *Bailhere's Clin. Haematol,* 1997; 10:691-709; Deegan P B, et al., *Blood Cells Mol Dis,* 2005; 35:259-67; Beutler, E, et al., *J Exp Med,* 1976; 143:975-80). An ELISA for detection of antibodies to aglucerase in which the active component is modified glucocerebrosidase has also been reported (Richards S M, et al., *Blood,* 1993; 82:1402; Rosenberg, M. et al, *Blood,* 1999; 93: 2081-2088). However, these assays do not directly detect lysosomal enzyme activity, and instead detect levels of indirect markers of disease.

Thus, there is a continuing need for improving the methods and compositions for detecting lysosomal disorders.

SUMMARY OF THE INVENTION

Improved compositions and processes for detecting enzymatic reactions using detection systems such as mass spectrometry, immunoassay, and high performance liquid chromatography are provided according to embodiments of the present invention.

The invention provides chemical compounds useful for assessing the level of lysosomal enzyme activity in a sample. Testing of lysosomal enzyme activity is useful, for example, when screening for metabolic disorders in newborns as well as when assessing an individual having a medical condition affecting enzyme activity or one undergoing a medical treatment such as enzyme replacement therapy, gene therapy, or bone marrow transplantation. The chemical compounds described herein include substrates for target enzymes and related molecules useful as controls or standards in enzyme assays.

An inventive substrate has the general formula A-($B^1$-$B^2$-$B^3$-$B^4$) where A is a monosaccharide or a disaccharide and $B^1$ is a $C_1$-$C_{20}$ alkyl, $C_1$-$C_{20}$ having a substituted $C_6$-$C_{20}$ aryl, $C_6$-$C_{20}$ heterocyclic containing a heteroatom of N, O or S; $B^2$ is an amino acid; 2,6-diaminohexanoic acid; or

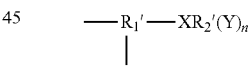

where $R_1'$ is a $C_1$-$C_{20}$ alkyl; $C_4$-$C_{20}$ ether; $C_1$-$C_{20}$ alkyl having a substituent of N, O, or S; heteroatom $C_6$-$C_{20}$ aryl, $C_1$-$C_{20}$ carbonyl, $C_1$-$C_{20}$ amidyl, $C_1$-$C_{20}$ ether, $C_6$-$C_{20}$ aryl, $C_6$-$C_{20}$ heterocyclic containing a heteroatom of N, O, or S; X is a nullity, oxygen, sulfur, or nitrogen; $R_2'$ is a nullity or $C_1$-$C_{20}$ alkyl, $C_4$-$C_{20}$ ether; $C_1$-$C_{20}$ alkyl having a substituent of N, O, or S; $C_1$-$C_{20}$ ester; $C_1$-$C_{20}$ alcohol; $C_1$-$C_{20}$ alkenyl; heteroatom $C_6$-$C_{20}$ aryl, $C_6$-$C_{20}$ heterocyclic containing a heteroatom of N, O or S; Y is a carbon, nitrogen, oxygen, or sulfur nucleophilic group; and n is an integer between 1 and 30.

$B^3$ is

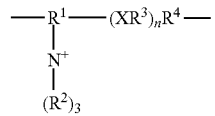

where $R^1$ is a $C_1$-$C_{20}$ alkyl; $C_4$-$C_{20}$ ether; $C_1$-$C_{20}$ alkyl having a substituent of N, O, or S; heteroatom $C_6$-$C_{20}$ aryl, $C_1$-$C_{20}$ carbonyl, $C_1$-$C_{20}$ amidyl, $C_1$-$C_{20}$ ether, $C_6$-$C_{20}$ aryl, $C_6$-$C_{20}$ heterocyclic containing a heteroatom of N, O, or S; $R^2$ is independently in each occurrence a H, a $C_1$-$C_{20}$ alkyl, a $C_2$-$C_{20}$ alkyl having a substituent of $C_1$-$C_{20}$ alkyl; X is independently in each occurrence a nullity, oxygen, sulfur, or nitrogen; $R^3$ is independently in each occurrence a nullity, $C_1$-$C_{20}$ alkyl, $C_1$-$C_{20}$ having a substituted $C_6$-$C_{20}$ aryl, $C_6$-$C_{20}$ heterocyclic containing a heteroatom of N, O or S; n is an integer between 0 and 30, inclusive; $R^4$ is independently in each occurrence a nullity, $C_1$-$C_{20}$ alkyl, $C_1$-$C_{20}$ having a substituted $C_6$-$C_{20}$ aryl, $C_1$-$C_{20}$ carbonyl, $C_1$-$C_{20}$ amidyl, $C_1$-$C_{20}$ ether, $C_6$-$C_{20}$ aryl, $C_6$-$C_{20}$ heterocyclic containing a heteroatom of N, O, or S; and $B^4$ is a nullity or $C_1$-$C_{20}$ alkyl, $C_4$-$C_{20}$ ether; $C_1$-$C_{20}$ alkyl having a substituent of N, O, or S; $C_1$-$C_{20}$ ester; $C_1$-$C_{20}$ alcohol; $C_1$-$C_{20}$ alkenyl; heteroatom $C_6$-$C_{20}$ aryl, $C_6$-$C_{20}$ heterocyclic containing a heteroatom of N, O or S.

Also provided are compounds of the general formula, which are useful, for example, as controls or standards in enzyme assays:

$$B^1\text{-}B^2\text{-}B^3\text{-}B^4 \quad (I)$$

where $B^1$ is a $C_1$-$C_{20}$ alkyl, $C_1$-$C_{20}$ having a substituted $C_6$-$C_{20}$ aryl, $C_6$-$C_{20}$ heterocyclic containing a heteroatom of N, O or S; $B^2$ is an amino acid; 2,6-diaminohexanoic acid; or

where $R_1'$ is a $C_1$-$C_{20}$ alkyl; $C_4$-$C_{20}$ ether; $C_1$-$C_{20}$ alkyl having a substituent of N, O, or S; heteroatom $C_6$-$C_{20}$ aryl, $C_1$-$C_{20}$ carbonyl, $C_1$-$C_{20}$ amidyl, $C_1$-$C_{20}$ ether, $C_6$-$C_{20}$ aryl, $C_6$-$C_{20}$ heterocyclic containing a heteroatom of N, O, or S; X is a nullity, oxygen, sulfur, or nitrogen; $R_2'$ is a nullity or $C_1$-$C_{20}$ alkyl, $C_4$-$C_{20}$ ether; $C_1$-$C_{20}$ alkyl having a substituent of N, O, or S; $C_1$-$C_{20}$ ester; $C_1$-$C_{20}$ alcohol; $C_1$-$C_{20}$ alkenyl; heteroatom $C_6$-$C_{20}$ aryl, $C_6$-$C_{20}$ heterocyclic containing a heteroatom of N, O or S; Y is a carbon, nitrogen, oxygen, or sulfur nucleophilic group; and n is an integer between 1 and 30.

$B^3$ is

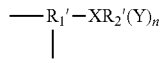

where $R^1$ is a $C_1$-$C_{20}$ alkyl; $C_4$-$C_{20}$ ether; $C_1$-$C_{20}$ alkyl having a substituent of N, O, or S; heteroatom $C_6$-$C_{20}$ aryl, $C_1$-$C_{20}$ carbonyl, $C_1$-$C_{20}$ amidyl, $C_1$-$C_{20}$ ether, $C_6$-$C_{20}$ aryl, $C_6$-$C_{20}$ heterocyclic containing a heteroatom of N, O, or S; $R^2$ is independently in each occurrence a H, a $C_1$-$C_{20}$ alkyl, a $C_2$-$C_{20}$ alkyl having a substituent of $C_1$-$C_{20}$ alkyl; X is independently in each occurrence a nullity, oxygen, sulfur, or nitrogen; $R^3$ is independently in each occurrence a nullity, $C_1$-$C_{20}$ alkyl, $C_1$-$C_{20}$ having a substituted $C_6$-$C_{20}$ aryl, $C_6$-$C_{20}$ heterocyclic containing a heteroatom of N, O or S; n is an integer between 0 and 30, inclusive; $R^4$ is independently in each occurrence a nullity, $C_1$-$C_{20}$ alkyl, $C_1$-$C_{20}$ having a substituted $C_6$-$C_{20}$ aryl, $C_1$-$C_{20}$ carbonyl, $C_1$-$C_{20}$ amidyl, $C_1$-$C_{20}$ ether, $C_6$-$C_{20}$ aryl, $C_6$-$C_{20}$ heterocyclic containing a heteroatom of N, O, or S; and $B^4$ is a nullity or $C_1$-$C_{20}$ alkyl, $C_4$-$C_{20}$ ether; $C_1$-$C_{20}$ alkyl having a substituent of N, O, or S; $C_1$-$C_{20}$ ester; $C_1$-$C_{20}$ alcohol; $C_1$-$C_{20}$ alkenyl; heteroatom $C_6$-$C_{20}$ aryl, $C_6$-$C_{20}$ heterocyclic containing a heteroatom of N, O or S.

DETAILED DESCRIPTION OF THE PREFERRED EMBODIMENTS

Figure 1:
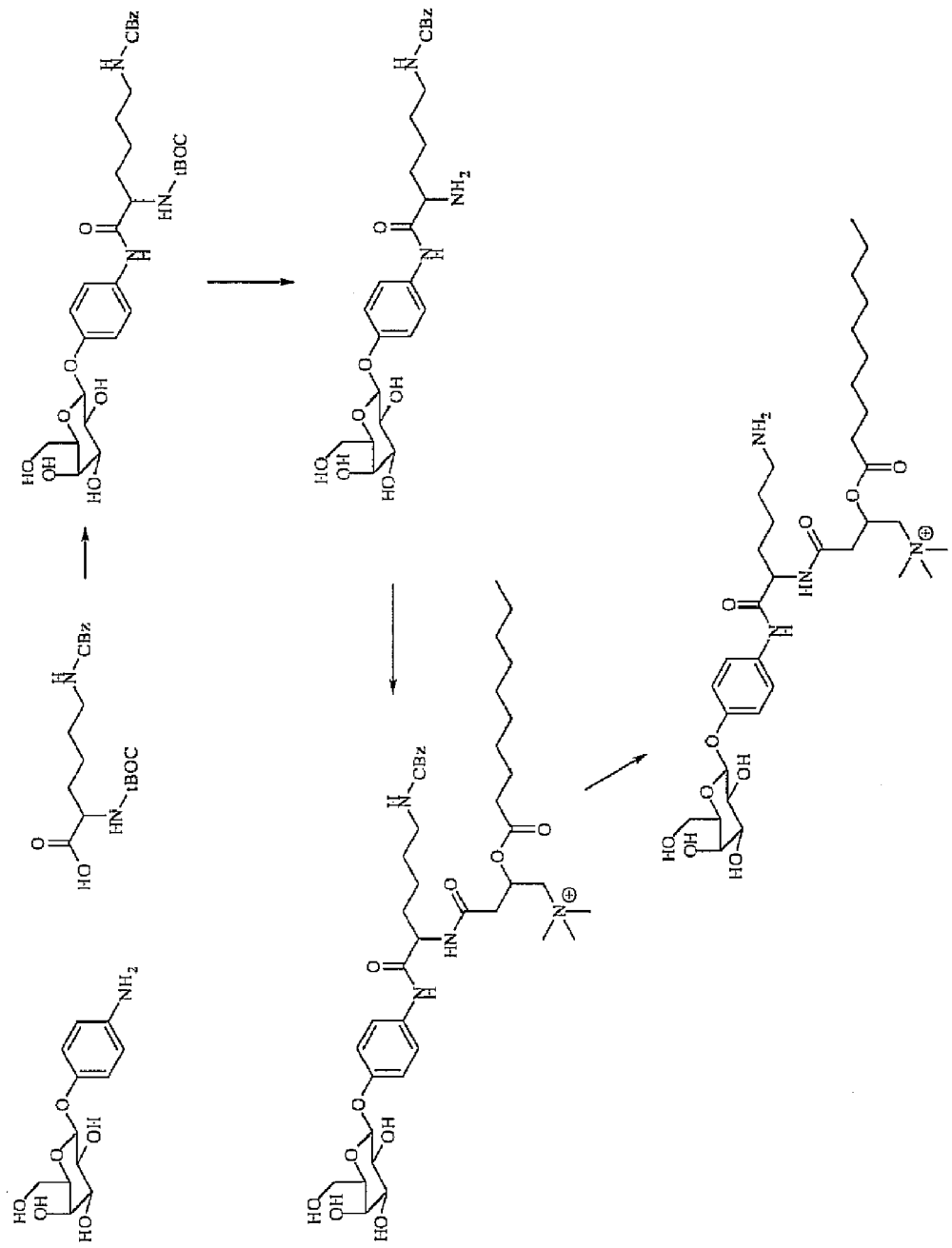
FIG. 1 is an exemplary substrate structure for detecting lysosomal storage disorders and illustrative method of synthesis.

The present invention has utility as an analytical reagent composition for detecting acid hydrolase enzyme activity, such as lysosomal enzyme activities associated with lysosomal storage disorders. Through the application of enzyme substrates and related compounds useful as experimental controls or standards, that are readily dissolvable in solutions adaptable for analytical methods such as mass spectrometry, HPLC and immunoassay, detecting enzyme activities associated with lysosomal storage diseases is more practical and less cumbersome.

The present invention provides substrates specific for lysosomal enzymes illustratively including acid α-galactosidase A (GLA), acid β-glucocerebrosidase (ABG), galactocerebroside α-galactosidase (GALC) and acid α-glucosidase (GAA). The action of these enzymes toward inventive substrates is used to measure the corresponding enzyme activities in a sample, and thus, these substrates can be used to detect lysosomal storage disorders including Fabry (GLA), Gaucher (ABG), Krabbe (GALC) and Pompe (GAA).

An inventive substrate has the general formula of A-($B^1$-$B^2$-$B^3$-$B^4$) where A is a monosaccharide or a disaccharide and $B^1$ is a $C_1$-$C_{20}$ alkyl, $C_1$-$C_{20}$ having a substituted $C_6$-$C_{20}$ aryl, $C_6$-$C_{20}$ heterocyclic containing a heteroatom of N, O or S; $B^2$ is an amino acid; 2,6-diaminohexanoic acid; or

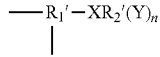

where $R_1'$ is a $C_1$-$C_{20}$ alkyl; $C_4$-$C_{20}$ ether; $C_1$-$C_{20}$ alkyl having a substituent of N, O, or S; heteroatom $C_6$-$C_{20}$ aryl, $C_1$-$C_{20}$ carbonyl, $C_1$-$C_{20}$ amidyl, $C_1$-$C_{20}$ ether, $C_6$-$C_{20}$ aryl, $C_6$-$C_{20}$ heterocyclic containing a heteroatom of N, O, or S; X is a nullity, oxygen, sulfur, or nitrogen; $R_2'$ is a nullity or $C_1$-$C_{20}$ alkyl, $C_4$-$C_{20}$ ether; $C_1$-$C_{20}$ alkyl having a substituent of N, O, or S; $C_1$-$C_{20}$ ester; $C_1$-$C_{20}$ alcohol; $C_1$-$C_{20}$ alkenyl; heteroatom $C_6$-$C_{20}$ aryl, $C_6$-$C_{20}$ heterocyclic containing a heteroatom of N, O or S; Y is a carbon, nitrogen, oxygen, or sulfur nucleophilic group; and n is an integer between 1 and 30.

$B^3$ is

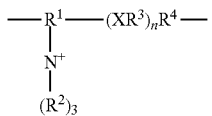

where $R^1$ is a $C_1$-$C_{20}$ alkyl; $C_4$-$C_{20}$ ether; $C_1$-$C_{20}$ alkyl having a substituent of N, O, or S; heteroatom $C_6$-$C_{20}$ aryl, $C_1$-$C_{20}$ carbonyl, $C_1$-$C_{20}$ amidyl, $C_1$-$C_{20}$ ether, $C_6$-$C_{20}$ aryl, $C_6$-$C_{20}$ heterocyclic containing a heteroatom of N, O, or S; $R^2$ is independently in each occurrence a H, a $C_1$-$C_{20}$ alkyl, a $C_2$-$C_{20}$ alkyl having a substituent of $C_1$-$C_{20}$ alkyl; X is independently in each occurrence a nullity, oxygen, sulfur, or nitrogen; $R^3$ is independently in each occurrence a nullity, $C_1$-$C_{20}$ alkyl, $C_1$-$C_{20}$ having a substituted $C_6$-$C_{20}$ aryl, $C_6$-$C_{20}$ heterocyclic containing a heteroatom of N, O or S; n is an integer between 0 and 30, inclusive; $R^4$ is independently in each occurrence a nullity, $C_1$-$C_{20}$ alkyl, $C_1$-$C_{20}$ having a substituted $C_6$-$C_{20}$ aryl, $C_1$-$C_{20}$ carbonyl, $C_1$-$C_{20}$ amidyl, $C_1$-$C_{20}$ ether, $C_6$-$C_{20}$ aryl, $C_6$-$C_{20}$ heterocyclic containing a heteroatom of N, O, or S; and $B^4$ is a nullity or $C_1$-$C_{20}$ alkyl, $C_4$-$C_{20}$ ether; $C_1$-$C_{20}$ alkyl having a substituent of N, O, or S; $C_1$-$C_{20}$ ester; $C_1$-$C_{20}$ alcohol; $C_1$-$C_{20}$ alkenyl; heteroatom $C_6$-$C_{20}$ aryl, $C_6$-$C_{20}$ heterocyclic containing a heteroatom of N, O or S.

Specificity of the inventive substrate for a particular lysosomal enzyme is provided in part by structural variations in the sugar moiety A such as A being a monosaccharide or a disaccharide. Exemplary sugar moieties include α-D-Glucose for detecting Pompe disease; β-D-Glucose for detecting Gaucher disease; α-D-Galactose for detecting Fabry disease; and β-D-Galactose for detecting Krabbe disease.

$B^1$ is a linker moiety which functions to allow conjugation of the sugar moiety A to the remaining structure of the substrate. $B^1$ also functions as a spacer between the sugar moiety A and the remaining structure of the substrate so as to provide flexible access for a target enzyme. The linker arm $B^1$ can be designed so as to confer relatively hydrophilic characteristics. Particularly, the linker arm $B^1$ can have a hydrophenol structure. Thus, an inventive substrate of the general formula of A-$B^1$-$B^2$-$B^3$-$B^4$ can be hydrophilic in a solvent such as pure methanol or pure ethanol. The $B^1$-$B^2$-$B^3$-$B^4$ moiety in toto generally is hydrophilic. As such, the inventive substrates can be soluble in aqueous buffer systems.

$B^2$ provides a nucleophilic group(s) for interactions with a solid support or detectable tag, such as a fluorescent tag. Preferably, $B^2$ is a derivative of an alkyl diamino acid, such as 2,6-diaminohexanoic acid. In the case of 2,6-diaminohexamoic acid, the 6-amino group optionally serves as a nucleophile for binding to a solid support or detectable tag.

A quaternary ammonium group is a component of $B^3$. Upon an enzymatic reaction, a cleaved product of $B^1$-$B^2$-$B^3$-$B^4$ carries with it a permanent positive charge located on the $B^3$. This property results in robust signal in tandem mass spectrometry analysis. Additionally, the permanent charge makes the inventive substrate more soluble in aqueous solutions so as to avoid the need for using solvents such as chloroform. In comparison to previously described substrates, a substrate according to the present invention is generally more hydrophilic and requires less or no need for detergents. This results in simplified assay procedures because, like the use of chloroform, the use of detergents can require cumbersome clean up steps including the labor-intensive liquid-liquid and solid phase extractions.

An inventive substrate is structurally terminated by a $B^4$ group. $B^4$ can be structurally tailored to provide different chain lengths. Such different chain lengths are useful for distinguishing different substrates, as well as enzymatic products thereof, from each other in enzyme assays. For example, in mass spectrometry, a substrate containing a 13 carbon atom chain has a different mass-to-charge ratio than a substrate containing a 14 carbon atom chain and as such, substrates containing 13 carbon atom or 14 carbon atom chains can be distinguished. Similarly, in immunoassay formats, substrates having differing chain lengths can be distinguished using antibodies selective for particular chemical moieties.

In one embodiment, the invention provides a reagent of formula A-$B^1$-$B^2$-$B^3$-$B^4$ wherein A is a monosaccharide or a disaccharide and preferably an aldohexose or a ketohexose; $B^1$ is a phenol, a nitrophenol, or a phenyl ester such as a phenyl benzoate; $B^2$ contains an alkyl group such as the amino acid lysine; $B^3$ contains a pendent quaternary ammonium cation extending from structure that prior to condensation to $B^1$ alone or also with a $B^4$ tail is carnitine.

The present invention provides methods for detecting enzyme activity. The activity of a particular enzyme can be assessed by its capability or rate of acting on a cognate substrate to product enzymatic products. In the case of an inventive substrate, action of a target enzyme on substrate A-$B^1$-$B^2$-$B^3$-$B^4$ results in generation of two products: A and $B^1$-$B^2$-$B^3$-$B^4$. By determining the amount of an enzymatic product, such as $B^1$-$B^2$-$B^3$-$B^4$, in a sample, the activity of the target enzyme can be determined. For applications in which a quantitative assessment of $B^1$-$B^2$-$B^3$-$B^4$ amount is desired, a known amount of an internal standard corresponding to $B^1$-$B^2$-$B^3$-$B^4$, as is described in more detail below, can be included in the sample. As such, the invention provides compounds having the general formula of $B^1$-$B^2$-$B^3$-$B^4$.

The activities of certain lysosomal enzymes in the blood of an individual can be used to test whether that individual has a lysosomal storage disorder. Therefore, the invention provides substrates for detecting medical conditions, in particular, lysosomal storage disorders such as Pompe disease, Gaucher disease, Fabry disease and Krabbe disease. For detecting Pompe disease, an exemplary sugar moiety is α-D-glucose and an exemplary $B^1$-$B^2$-$B^3$-$B^4$ portion is 4-aminophenyl-diaminohexanoyl-carnitinyl-alkyl chain with $B^4$ of 10-20 carbons. For detecting Gaucher disease, an exemplary sugar moiety is β-D-glucose and an exemplary $B^1$-$B^2$-$B^3$-$B^4$ portion is 4-aminophenyl-diaminohexanoyl-carnitinyl-alkyl with $B^4$ of 10-20 carbons in length. For detecting Fabry disease, an exemplary sugar moiety is α-D-galactose and an exemplary $B^1$-$B^2$-$B^3$-$B^4$ portion is 4-aminophenyl-diaminohexanoyl-carnitinyl-alkyl with $B^4$ of 10-20 carbons in length. For detecting Krabbe disease, an exemplary sugar moiety is β-D-galactose and an exemplary $B^4$ portion is 4-aminophenyl-diaminohexanoyl-carnitinyl-alkyl with $B^4$ of 10-20 carbons in length. A specific example of an inventive substrate specific for detecting Krabbe disease has a group A of β-D-Galactose, a group $B^1$ of a methylene, a group $B^2$ of an amidylaminoacyl group, a group $B^3$ of a amidyl terminating with a quaternary ammonium, and group $B^4$ of alkenyl alcohol with a carbon length of 12 to 20. A specific example of an inventive substrate for detecting Gaucher disease has a group A of β-D-Glucose, a group $B^1$ of a methylene, a group $B^2$ of an amidylaminoacyl group, a group $B^3$ of a amidyl terminating with a quaternary ammonium, and group $B^4$ of alkenyl alcohol with a carbon length of 12 to 20.

An inventive substrate can be tailored for assaying a variety of enzymes, in particular, enzymes associated with a disease state or birth detect, or one otherwise useful for medical purposes. Such tailoring is possible because a variety of monosaccharide and disaccharide groups can be present at A of the general formula $A-B^1-B^2-B^3-B^4$. Even for a newly identified target enzyme, once its specificity for monosaccharide and/or disaccharide groups is determined using routine methods, an inventive substrate can be readily prepared using guidance provided herein. Non-limiting examples of enzymes which can be assayed using an inventive substrate as described herein include acid α-galactosidase A, acid β-glucocerebrosidase, acid galactocerebroside α-galactosidase, acid sphingomyelinase, and acid α-glucosidase As it is envisioned in the present invention, one can synthesize substrates with different sugars, each specific to a particular lysosomal enzyme, and each having a different chain length in subgroup $B^2$ or $B^4$. This inventive system provides for optional multiplex assays where two or more lysosomal enzymes are analyzed in the same sample or sample receptacle using structurally similar yet enzyme specific substrates.

The present invention provides compounds that function as experimental controls or standards useful for assessing the amount of enzymatic product in a sample or sample receptacle. For use in mass spectrometry methods, an internal standard corresponding to a particular inventive substrate is structurally identical to its enzymatic product, except that the internal standard differs in mass-to-charge (m/z) ratio. Thus, the internal standards of the present invention include modified forms of enzymatic products, for example, stable isotope-labeled analogs of enzymatic products in which one or more atoms are replaced by corresponding atomic isotopes so as to create a shift in the mass. When the internal standard and enzymatic product are analyzed by mass spectrometry, the resulting spectrum reveals a spatial separation of the internal standard and enzymatic product, each represented by its own peak. The known amount of internal standard is reflected by peak magnitude at its known m/z ratio. The amount of enzymatic product can be assessed by comparison of peak magnitude at its known m/z, relative to the peak magnitude of the internal standard. An example of isotopic labeling to produce an internal standard is the replacement of $^1H$ on an acyl group of $B^4$ with $^2D$. As a result, a "heavier" internal standard molecule with the substituted $^2D$ has a different m/z from the enzymatic product, as detected on a mass spectrum.

In a particular embodiment, an internal standard is labeled with deuterium to cause a mass change of 3 to 9 Daltons from the corresponding cleaved product. In another particular embodiment, a combined $B^2-B^3-B^4$ subgroup is a lysine-acylcarnitine with a positively charged quaternary ammonium moiety and the acyl tail is of carbon length from 12 to 18.

In one embodiment the inventive substrates are labeled with a detectable tag. Many fluorescent probes are recognized in the art as useful for labeling reactive amines. A particularly sensitive target for specific labeling of biomolecules is the side chain amino group of lysine. A preferred embodiment of the inventive substrates includes a lysine residue at position $B^2$ that possess this active terminal amino group. Illustrative examples of detectable tags suitable for labeling the inventive substrates include fluorophores such as isothiocyanates, dansyl and other sulfonyl chlorides, 7-nitrobenz-2-oxa-1,3-diazole derivatives, fluorescamine, and the like.

An inventive substrate can be used in a variety of physical formats, for example, in solution as well as linked or immobilized to solid supports. A solid support can be composed of a natural or synthetic material, an organic or inorganic material, such as a polymer, resin, metal or glass, and combinations thereof. A suitable solid support can have a variety of physical formats, which can include for example, a membrane; column; a hollow, solid, semi-solid, pore or cavity-containing particle such as a bead; a gel; a fiber, including a fiber optic material; a matrix and sample receptacle. Non-limiting examples of sample receptacles include sample wells, tubes, capillaries, vials and any other vessel, groove or indentation capable of holding a sample. A sample receptacle can be contained on a multi-sample platform, such as a microplate, slide, microfluidics device, and the like. Many suitable particles are known in the art and illustratively include Luminex®-type encoded particles, encoded fiber optic particles, magnetic particles, and glass particles. Covalent interaction of an inventive substrate and/or enzymatic cleavage product thereof with a solid support is useful for retaining the substrate and/or product during washing procedures performed in some assay formats, thus, producing a robust and accurate signal of enzymatic activity.

When use of a solid support is desired for an assay format, the presence of the exemplary lysine group $B^2$ can be used, for example, for covalent bonding to high-binding solid supports. High binding solid supports are surfaces having exposed moieties that are chemically active or otherwise capable of covalent or high affinity binding to an inventive substrate or internal standard. As an example, Corning Life Sciences produces high-binding microwell plates that are irradiated to break the benzene ring and produce exposed carboxylic acids. These carboxylic acids are amenable to nucleophilic attack such as by the terminal amino group on the lysine derivative component of a preferred embodiment substrate. This reaction is rapid and produces a tight interaction between the substrate/product and the high-binding surface.

The methods described herein can be performed in a multiplexed format such that a plurality of samples are assayed simultaneously. An illustrative multiplexed format involves using physically and/or chemically coded particles. Use of coded particles in multiplexed formats has been described, for example, in U.S. Pat. No. 6,649,414 and U.S. Pat. No. 6,939,720. Because the codes allow particles to be distinguished from each other, a plurality of distinct particles can be present in a single reaction mixture, allowing a plurality of different samples or different enzymes to be assayed simultaneously. Codes on particles can correspond, for example, to sample origins, particular enzymes to be assayed, particular substrates present, and the like, depending on the experimental goal of the user.

A sample useful in the methods of the invention contains or is suspected of containing one or more target enzymes. Target enzymes can be contained in samples obtained from an individual, as well as from laboratory materials, such as cell lines, and synthetic protein sources. Exemplary sample sources include tissue homogenates; cell culture lysates; biological fluids including urine, blood in liquid or dry form, tears, saliva, and cerebrospinal fluid. A sample can be further fractionated, if desired, to a fraction containing particular cell types. For example, a blood sample can be fractionated into serum or into fractions containing particular types of blood cells such as red blood cells or white blood cells (leukocytes). If desired, a sample can be a combination of samples from a subject such as a combination of a tissue and fluid sample, and the like. In a specific embodiment, the sample is blood, which can be, for example, whole blood or a blood fraction thereof, or reconstituted from a dry blood sample.

Methods for obtaining samples that preserve the activity or integrity of molecules in the sample are well known to those skilled in the art. Such methods include the use of appropriate buffers and/or inhibitors, including nuclease, protease and phosphatase inhibitors, which preserve or minimize changes in the molecules in the sample. Such inhibitors include, for example, chelators such as ethylenediamine tetraacetic acid (EDTA), ethylene glycol bis(P-aminoethyl ether)N,N,N1,N1-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Appropriate buffers and conditions for isolating molecules are well known to those skilled in the art and can be varied depending, for example, on the type of molecule in the sample to be characterized (see, for example, Ausubel et al. Current Protocols in Molecular Biology (Supplement 47), John Wiley & Sons, New York (1999); Harlow and Lane, Antibodies: A Laboratory Manual (Cold Spring Harbor Laboratory Press (1988); Harlow and Lane, Using Antibodies: A Laboratory Manual, Cold Spring Harbor Press (1999); Tietz Textbook of Clinical Chemistry, 3rd ed. Burtis and Ashwood, eds. W.B. Saunders, Philadelphia, (1999)). A sample also can be processed to eliminate or minimize the presence of interfering substances.

Samples in the form of a dry blood spot are commonly used when screening blood from newborns and children patients. To prepare these samples, blood is collected and retained on a filter paper. For analysis, the dried blood is eluted from the filter paper into an aqueous solution, which generally contains a buffer such as phosphate buffer saline and a protease inhibitor. Specific examples of protease inhibitor conditions include for example, include one or more of the following: AEBSF hydrochloride in a final concentration of 50 to 400 µg/ml, EDTA disodium dehydrate in a final concentration of 0.2 to 25 mg/ml, leupeptin hemisulfate in a final concentration of 0.5 to 1 µg/ml, and pepstatin A in a final concentration of 0.5 to 1 µg/ml. The use of a universal assay solution to extract a single dry blood sample, or other type of sample, for subsequent distribution into multiple assay reactions can be used for automatic and high throughput screening. A single extraction of a dry sample avoids the need to obtain several sample punches from the same sample, or to collect aliquots of other sample sources and accordingly reduces variation caused by inhomogeneous distribution of blood on the filter paper and errors in sample transfer. When using dry samples, extraction efficiency may vary with the different enzymes being analyzed. In these and other types of samples, the target enzymes may have different levels of activities when contained in different assay solutions. Composition of the inventive universal assay solution is optionally chosen such that each enzyme to be tested is active.

The inventive substrates and products can be used in a variety of assay formats. The substrate can be detected in an assay when it is desired to observe substrate consumption during an enzymatic assay, while the product can be detected in the assay when it is desired to observe its formation during an enzymatic assay. Both substrate and product can be detected when it is desired to observe the enzymatic reaction from both perspectives, for example, to confirm that the amount of product produced correlates with the amount of substrate consumed.

For example, the amount of substrate $A-B^1-B^2-B^3-B^4$ or product $B^1-B^2-B^3-B^4$ can be detected using established tandem mass spectrometry procedures. An exemplary enzyme assay employing mass spectrometry can be performed as follows. A sample is incubated with an inventive substrate for a time period that allows formation of an enzymatic product. During the incubation period, the substrate is cleaved by a target enzyme present in a blood sample to form a respective $B1-B2-B3-B4$ product. The reaction is then quenched by adding a reagent that precipitates protein components. Exemplary reagents include alcohol, acetonitrile and dilute trifluoro acetic acid. A portion of the incubation mixture is then transferred to a new assay vessel. Optionally, a dilution reagent such as methanol, acetonitrile, water-methanol mixtures or water-acetonitrile can be added to dilute the transferred portion. The sample so diluted reduces the amount of endogenous competing material so as to relatively increase the sensitivity of the tandem mass spectrometry analysis. Other types of reagents are selected by those skilled in the art to be compatible with tandem mass spectrometry analysis.

The diluted sample is directly injected into the tandem mass spectrometer either manually or automatically with the aid of autosamplers and liquid handlers. If desired, the sample can be derivatized prior to analysis. Reagents are selected to be non-hostile to the MS/MS system. For example, suitable solvents lack detergents and corrosive agents, such as chloroform. Pure ethanol and pure methanol are often used simply because they easily vaporized upon mechanical drying processes.

The tandem mass spectrometer can be set to simultaneously detect the added substrate, the corresponding resulting enzymatic product and the corresponding internal standards. Such detection is accomplished by means of parent ion scans, precursor ion scans or multiple reaction monitoring scans.

The amount of substrate $A-B^1-B^2-B^3-B^4$ or product $B^1-B^2-B^3-B^4$ formed during an enzymatic assay also can be detected using antibodies and other target-specific binding molecules. For immunoassays, an antibody can be used to detect the substrate, product or both. Antibodies useful in such methods can be specific, such that they recognize individual substrates, or non-specific, such that they recognize many or all substrates. An illustrative example is an antibody generated to the combination B1-B2 nitrophenol-lysine.

The antibody is illustratively produced in animals including mouse, rat, rabbit, horse, donkey, or other suitable animal used for the production of antibodies. In some applications, it is useful to label an antibody with a detectable tag, such as a fluorescent tag. When using an unlabeled antibody, detection can be performed by using a secondary antibody that is specific for the species IgG of the primary antibody is labeled illustratively with a fluorescent marker such as rhodamine. It is appreciated in the art that other antibody detection systems are similarly operable in the instant invention such as horseradish peroxidase labeled antibodies, or alkaline phosphatase labeled antibodies.

When testing multiple enzymes in a single sample by providing multiple enzyme-specific substrates, antibodies that recognize and distinguish between the substrates, or products thereof, and be used. Complexes of antibodies bound to enzyme-specific substrates, or products thereof, can be distinguished from each other using many methods. In one scenario, samples containing target enzymes are contacted with substrates linked to particles in an assay solution. In this example, each particle is linked to a particular substrate, and there are multiple particles representing each substrate. The target enzymes act on the substrates to produce products A and $B^1-B^2-B^3-B^4$. The $B^1-B^2-B^3-B^4$ product remains bound to the particle, while the A product is released into solution. Antibodies that recognize specific $B^1-B^2-B^3-B^4$ products are then contacted with the assay solution. The antibodies will bind to the products, if produced during the enzymatic assay, to produce particles having bound antibodies. To distinguish different products contained on the particles, antibodies having different product specificities can have different detectable moieties, such as different fluorescent tags. As an alternative to detecting enzymatic products, antibodies that recognize substrate $A$-$B^1$-$B^2$-$B^3$-$B^4$ can be used to detect substrate remaining on the beads after incubation with enzymes. In this situation, either product A or $B^1$-$B^2$-$B^3$-$B^4$ would remain attached to the bead, if an enzymatic reaction occurred. In either case the selected substrate specific antibody would not significantly cross-react with product attached to the bead.

In another scenario, samples containing target enzymes are contacted with substrates linked to encoded particles in an assay solution. The encoded particles have a feature, such as a bar code or optical profile, which allows them to be distinguished from each other. For example, encoded particles can have different bar codes corresponding to different target enzyme substrates. In the assay, the target enzymes act on the substrates to produce products A and $B^1$-$B^2$-$B^3$-$B^4$. The $B^1$-$B^2$-$B^3$-$B^4$ would remain bound to the particle, while the A product would be released into solution, or visa versa. Antibodies that recognize specific products are then contacted with the assay solution. Because the encoding of the particle indicates which substrate is attached to the particle, antibodies need not be specific for particular products, and thus one type of antibody can be used to detect products derived from multiple different substrates. Such non-specific antibodies will bind to the products, if produced during the enzymatic assay, to produce particles having bound antibodies. Particles having bound antibodies are then distinguished from those without antibodies, for example, by detecting a tag on the antibodies or physical behavior of the particles. The different products contained on the antibody-bound particles can be determined based on the encoding of each particle.

As another example of an immunoassay format, antibodies directed to particular substrates are generated. Following quenching of an enzymatic reaction, the reaction solution is transferred to a high-binding microtiter plate whereby the reactive $B^2$ moiety covalently attaches to the plate via a terminal amino group. The enzyme and assay solution components are removed by washing. The specific primarily antibody is then incubated in each assay well followed by subsequent washing to remove unbound antibody. A secondary antibody is optionally used for detection and quantitation. The more product formed per unit time of initial reaction the greater the activity of the measured enzyme.

In an alternative immunoassay format, an antibody specific for the $B^1$-$B^2$ subgroup is optionally used as a capture antibody on the surface of the microtiter plate in a standard sandwich ELISA assay. A primary antibody with a unique epitope on the product such as one directed to the $B^4$ moiety (or the $B^4$ moiety is modified with a specific binding pair member such as biotin) is used for detection. As is recognized in the art, a labeled secondary antibody is optionally used for detection as described above.

In an additional immunoassay format, an exemplary antibody reacts with the α-D-glucose A group bound to the inventive hydrophenol $B^1$ moiety. The substrate is attached to a solid support using a lysine $B^2$ moiety. Alternatively, the substrate is provided in solution, the reaction is transferred to a sample receptacle, in which Following quenching of an exemplary enzymatic reaction, the reaction solution is transferred to a high-binding microtiter plate whereby the reactive $B^2$ moiety covalently attaches to the receptacle via a terminal amino group. As another alternative, a capture antibody specific for an alternate epitope on the inventive product/substrate is employed. The unreacted enzyme and buffer components are removed by washing. The antibody specific to the $A$-$B^1$-$B^2$ moiety is then incubated in each assay well for detection and quantitation of remaining substrate. The greater the substrate remaining after the initial enzyme reaction, the lower the activity of the enzyme.

The antibody is illustratively unlabeled and produced in animals including mouse, rat, rabbit, horse, donkey, or other suitable animal used for the production of antibodies. A secondary antibody that is specific for the species IgG of the primary antibody is labeled illustratively with a fluorescent marker such as rhodamine and subsequently used for detection of remaining substrate. It is appreciated in the art that other antibody detection systems are similarly operable in the instant invention such as horseradish peroxidase labeled antibodies, or alkaline phosphatase labeled antibodies.

In another example of a suitable immunoassay format, monoclonal mouse antibody specific for the exemplary the α-D-glucose A group bound to the inventive hydrophenol $B^1$ moiety and lysine $B^2$ moiety is itself labeled illustratively by a fluorescent marker. In this system multiple lysosomal enzymes are optionally simultaneously analyzed for activity toward a variety of specific substrates. An illustrative example includes a two enzyme system wherein inventive substrate are employed, one specific for GLA and another specific for GAA. Each substrate is simultaneously added to the reaction with the biological sample. As each substrate optionally contains a lysine $B^2$ group, both will similarly bind to the high-binding microtiter plate. Two antibodies, each specific for its respective inventive substrate are added to the microtiter plate following washing as above. Each antibody is illustratively labeled with a different fluorophore such as rhodamine or cyanine. As such the binding of each antibody is detected and quantitated without interference from the other, and the amount of each enzyme activity is detectable in the same well of the microtiter plate from the same sample.

Another illustrative assay format is performed using mass spectrometry. An assay for target enzymes is performed by first obtaining a sample illustratively including serum, plasma, whole blood, urea, saliva, other biological fluids or tissue lysates, recombinant or native purified enzyme in solution, or chemically or functionally modified enzyme in biological fluid or liquid medium. A portion of the filter paper sample is then excised and deposited in a non-binding assay tube or micro titer plate well to which an assay solution is added. The assay solution comprises aqueous buffers, a substrate, a standard, as well as protease inhibitors. The sample mixture is then incubated for a determined period of time in the range of 30 minutes to 20 hours at a particular temperature ranging from 30 to 41° C. Once incubation is complete, the enzymatic reaction is terminated by addition of a stopping solution. A stopping solution is illustratively 0.4 M glycine/NaOH pH 10.4 added at 6× reaction volume. Leonard R, et al., *J. Biol. Chem.*, 2006; 281:4867-75; Boot, R G, et al., *J. Biol. Chem.*, 2006; 282:1305-12. The amount of product formation is determined by transferring a known volume of sample to a high-binding assay tube or microtiter plate and incubated for 5 minutes to 2 hours. The unbound material is removed by washing. Detection of the intact substrates or products is illustratively performed using a coupled peroxidase enzyme approach. In a further scenario, the level of released glucose or galactose product is measured in real time by a coupled enzyme approach. A non-limiting example involves the release of glucose from an inventive substrate specific for alpha-glucosidase in diagnosis of Pompe disease. In this assay method glucose is reacted with glucose oxidase producing glucolactone and releasing hydrogen peroxide. The released hydrogen peroxide is detected by reaction with peroxidase to produce a fluorescent molecule that is measured on a standard fluorometer. Examples of suitable peroxidases are horseradish peroxidase or any other peroxidase known in the art. The hydrogen peroxide released by glucose oxidase interacts with a detector substrate molecule. The peroxidase catalyzes conversion of this substrate to a fluorescent product. A detector molecule suitable for use with the inventive substrates includes Amplex Red that is oxidized in to produce the fluorescent product resorufin. Amplex Red and kits for detecting free glucose are available from Invitrogen Corp. The increase in red fluorescent product is detected on a fluorometer set with an excitation wavelength at 571 and an emission wavelength at 585 with the band pass set at 5 nm. The greater amount of glycosidase activity the more rapidly the red fluorescent product is produced.

In a preferred embodiment multiple substrates for different lysosomal enzymes are generated with unique $B^1$-$B^4$ structure. This prevents product inhibition of one enzyme that is particularly important should the catalytic activity of one enzyme toward one inventive substrate be much greater than the catalytic activity of the other enzyme for its corresponding inventive substrate. This is additionally important in conditions where a single mutant glycosidase is being screened in a panel of substrates for 6 or more lysosomal enzymes. The product formed by the other lysosomal enzymes may inhibit the function of the lower activity enzyme such that its activity is not accurately measured. Thus, the specificity of the substrate and the product for each enzyme is appreciated to be optionally distinct.

When more than one enzyme is detected simultaneously by combining multiple substrates directed to respective enzymes, the substrates may differ not only in the type of sugar moiety which confers enzyme specificity, but also in the length of the $B^4$ tail moiety. This is particularly important with the use of MS/MS as a detection tool since the differentiated inventive substrate molecules having corresponding differentiated mass index correspond to various enzymes being examined.

The approach described for assaying enzymes using substrate reagents, immunoassay, HPLC, and mass spectrometry according to the present invention may be broadly applied. The multiplex techniques may be expanded to assay dozens or more enzymes simultaneously in a single reaction, obviating the need for multiple assays to assist in confirming diagnoses of rare disorders. The method may be used to measure several enzymes simultaneously when evaluating the rate of chemical flux through a specific biochemical pathway or for monitoring biochemical signaling pathways. Because of the high sensitivity of the ESI-MS detection employed, which requires only sub-microgram quantities of the substrate reagents per assay, the synthesis of several hundred substrate reagents on a low-gram scale becomes practical and economical.

In a preferred embodiment two lysosomal enzymes are simultaneously measured for activity by the use of inventive substrates. In an alternative embodiment 2-6 lysosomal enzymes are simultaneously measured.

As another exemplary format for use of the inventive substrates, the substrates can be labeled with the same fluorophore, but possess significant mass or charge characteristics that differentiate one from the other. The amount of product produced following an enzymatic cleavage reaction is detected by reversed phase high performance liquid choromatography (HPLC). Reactions are quenched by the addition of alcohol, acetonitrile or dilute trifluoro acetic acid. A portion of the incubation mixture is transferred to a new assay vessel to which is added a neat solution such as methanol, acetonitrile, water-methanol mixtures or water-acetonitrile.

The reaction products and unreacted substrate are separated on a 5 μm particle size $C_{18}$HPLC column and detected by a fluorescent detector or set of detectors. The amount of product is calculated based on a standard curve generated using increasing amounts of the relevant product.

It is appreciated in the art that multiple substrates for multiple enzymes are optionally simultaneously detected by the HPLC method. If substrates with sufficiently different mass or retention characteristics are used each product is resolvable in the HPLC column and can be quantified in a single assay. Alternatively, each substrate is labeled with a different fluorophore that has different or the same excitation or emission properties. Detection may be by a family of fluorescent detectors that can simultaneously quantify individual products from each other and their corresponding labeled substrate. Other methods of detection are similarly suitable and are known in the art.

FIG. 1 shows α-D-glucose, modified with a 4-aminophenyl group is reacted with a di-protected lysine group. Methods for di-protecting lysine are known in the art and illustrative examples are described in WO 01/27074. The intermediate A-$B^1$-$B^2$ is formed which is specifically deprotected at the alpha-amino group to provide a suitable reactive site for subsequent synthetic steps. Methods of site-specific deprotection are known in the art. The alkyl chain is then added. An exemplary alkyl chain is provided by dodecylcarnitine ($B^3$-$B^4$) which is synthetically added to the A-$B^1$-$B^2$ intermediate to form a full length substrate molecule (A-$B^1$-$B^2$-$B^3$-$B^4$). This substrate molecule is active as a GAA specific substrate and is optionally used in analyses involving mass spectrometry or other suitable assay and detection method. In another preferred embodiment, the 6-amino group on $B^2$ is deprotected so as to produce a similarly reactive substrate. It is appreciated in the art that synthesis of numerous derivatives of the above illustrated substrate are similarly achieved such as by varying the carbon chain on the acylcarnitine, altering the sugar A group or the $B^1$ group. Also, numerous derivatives of lysine ($B^2$) or other alkyl groups are similarly suitable.

Figure 2:
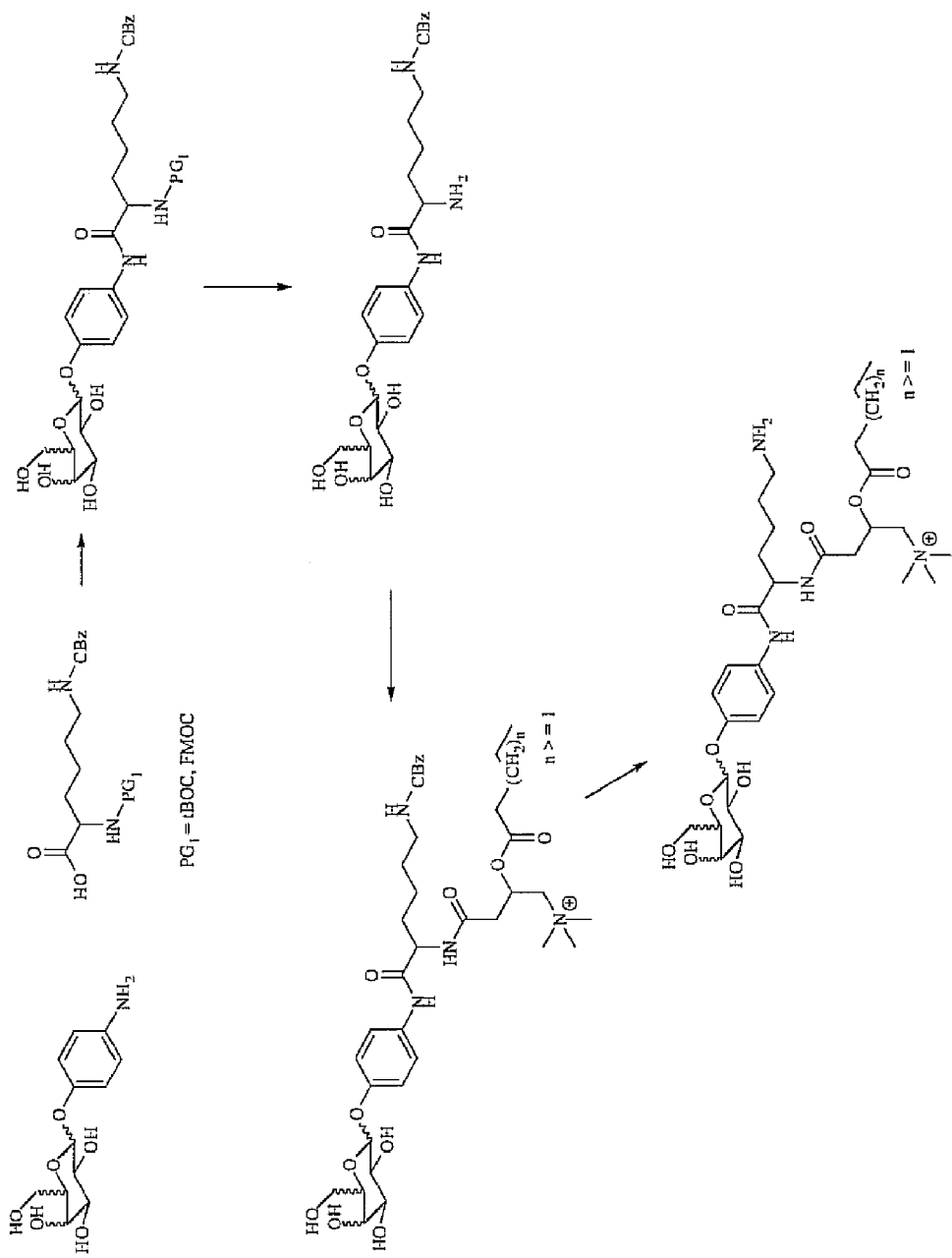
FIG. 2 is an exemplary substrate structure for detecting lysosomal storage disorders of general composition and an illustrative method of synthesis.

It is appreciated in the art that similar synthetic pathways are suitable for production of the inventive substrates. FIG. 2 depicts a synthetic pathway similar to FIG. 1 except for the protective groups and the choice of acylcarnitine whereby n is a value between 1 and 30. Preferably, n is between 1 and 20.

Figure 3:
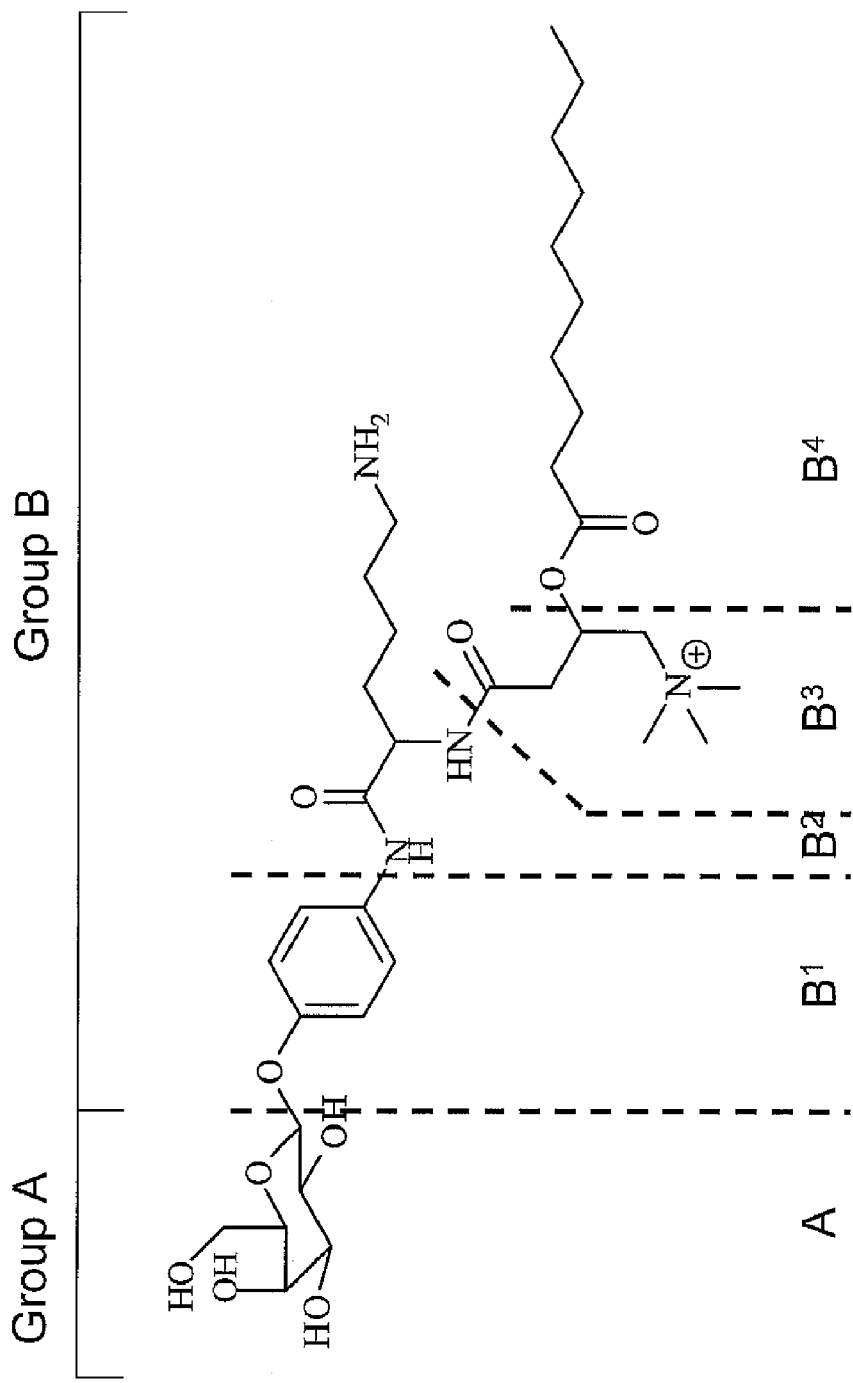
FIG. 3 is an exemplary substrate structure highlighting structural moieties.

FIG. 3 depicts an exemplary substrate structure for detecting lysosomal storage diseases. The structure is composed of a sugar (A) in the form of a glucose or a galactose and an aliphatic group B. Group B is further composed of a linker arm ($B^1$) in the form of a nitrophenyl, a $B^2$ subgroup of a lysine, a $B^3$ subgroup of a carnitinyl, and a $B^4$ subgroup in the form of an alkyl with carbon length in the range of 10 to 30. A quaternary ammonium cation located on the $B^3$ subgroup avoids the need of further ionization otherwise needed for mass spectrometry detection.

Figure 4:
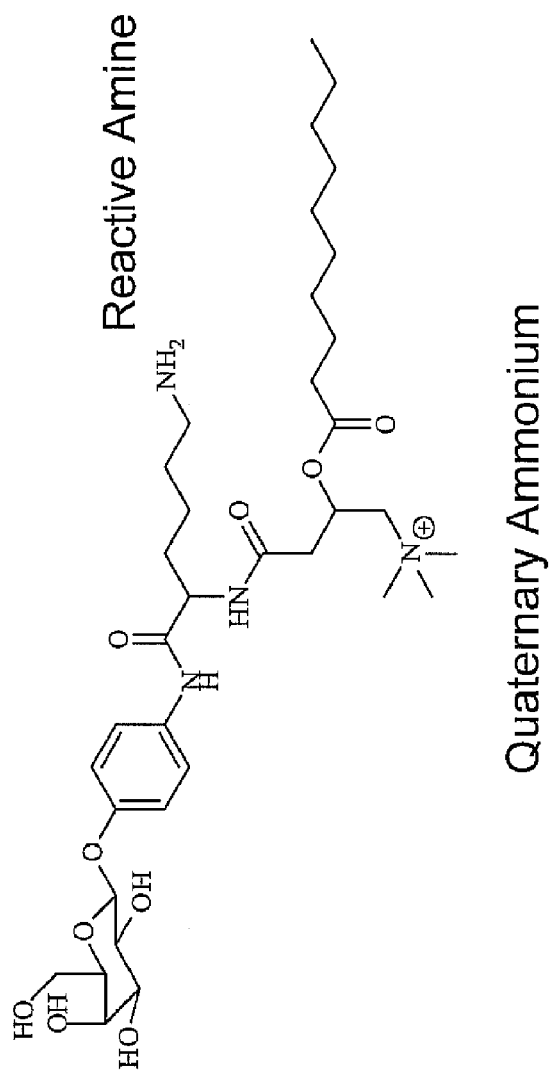
FIG. 4 is an exemplary substrate structure highlighting multiple functional centers amenable to multiple detection methods.

FIG. 4 depicts the multiple functional groups that provide multiple assay format detection of enzymatic activity. The terminal amino group on $B^2$ is capable of forming covalent bonds with carboxylic acids on solid supports. The presence of the quaternary ammonium on $B^3$ provides a permanently charged moiety such that subsequent ionization is not required for analysis by MS/MS providing a robust and easily detectable and quantifiable detection of lysosomal enzyme activity.

Figure 5:
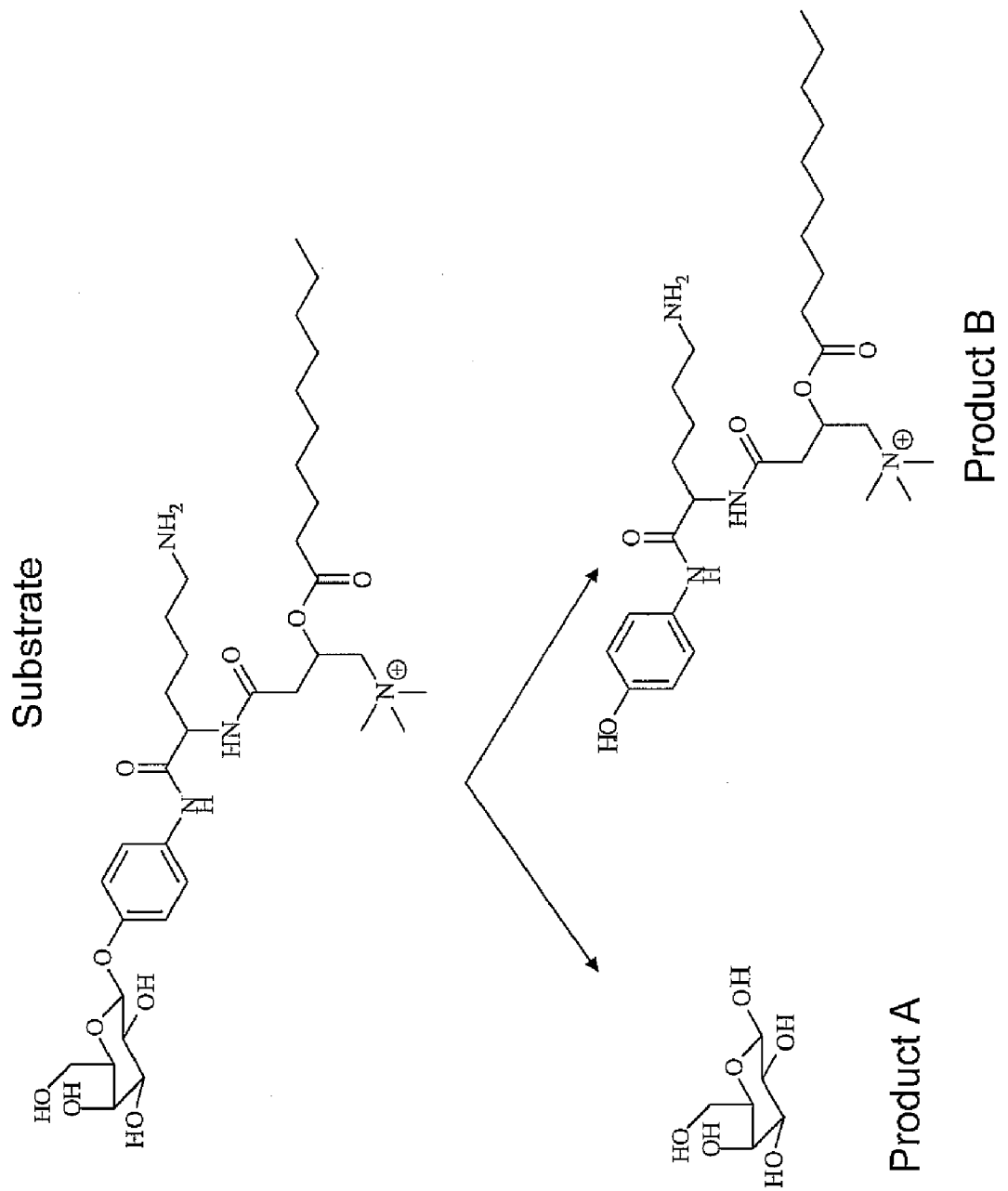
FIG. 5 is a generic enzymatic reaction scheme using an inventive substrate.

FIG. 5 demonstrates a generic enzymatic reaction using an inventive substrate. Upon specific affinity binding and enzymatic reaction, the substrate is cleaved into two groups, a sugar moiety A and an aliphatic group B. The group B is optionally composed of a nitrophenyl, a lysine, a carnitinyl, and long-chain alkyl moieties. Both groups are optionally then analyzed by MS/MS. An internal standard is also concurrently subject to the MS/MS analysis. The internal standard is an isotopically labeled analog of B with deuterium to replace hydrogen atom(s) on a methyl group. Alternatively, the deprotected terminal amino group on $B^2$ is reactive with a solid support such that the presence or absence of product is optionally detected using immunoassay methods. The deprotected terminal amine can also be derivatized with a fluorescent reagent for HPLC, or other suitable detection method.

Figure 6:
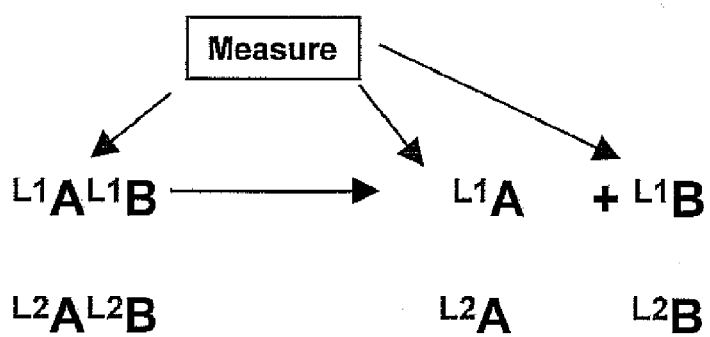
FIG. 6 is an alternative method of detecting enzymatic activities using double labeling of an inventive substrate.
Figure 7:
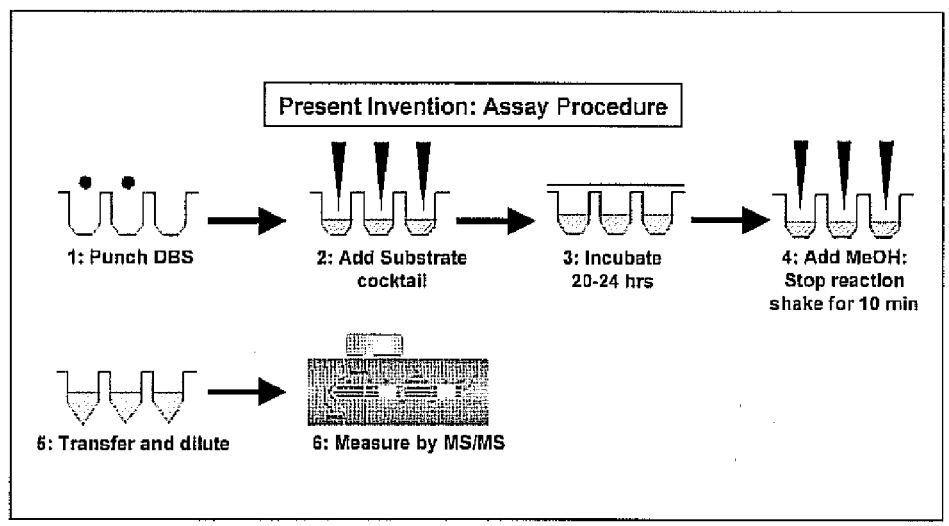
FIG. 7 is an inventive method of detecting enzymatic reactions using mass spectrometry that is advantageous in comparison to a prior art reference method.

FIG. 6 illustrates exemplary inventive methods depicting detection of enzymatic reactions using mass spectrometry that are advantageous in comparison to prior art methods.

In the prior art, lysosomal enzyme substrates each require a unique synthetic pathway. In contrast, the inventive substrates can be synthesized using a common synthetic pathway. Having a common synthetic pathway for two or more of the inventive substrates means significant savings in production environments due to shorter and less complex production processes and the use of common raw materials. The inventive substrates also can be rapidly synthesized relative to the prior art. Synthesis is accomplished in as little as three steps. Synthesis of a preferred inventive substrate with specificity for the lysosomal enzyme GAA (Pompe disease) is illustrated in FIG. 1.

It is further appreciated that the compound $B^1$-$B^2$-$B^3$-$B^4$ is also functional as an antagonist, an analytical control, or for clinical treatment of disease such as hypothyroidism, diabetes, and HIV. The $B^1$-$B^2$-$B^3$-$B^4$ molecule is: $B^1$ is a $C_1$-$C_{20}$ alkyl, $C_1$-$C_{20}$ having a substituted $C_6$-$C_{20}$ aryl, $C_6$-$C_{20}$ heterocyclic containing a heteroatom of N, O or S; $B^2$ is an amino acid; 2,6-diaminohexanoic acid; or

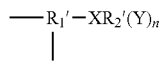

where $R^{1'}$ is a $C_1$-$C_{20}$ alkyl; $C_4$-$C_{20}$ ether; $C_1$-$C_{20}$ alkyl having a substituent of N, O, or S; heteroatom $C_6$-$C_{20}$ aryl, $C_1$-$C_{20}$ carbonyl, $C_1$-$C_{20}$ amidyl, $C_1$-$C_{20}$ ether, $C_6$-$C_{20}$ aryl, $C_6$-$C_{20}$ heterocyclic containing a heteroatom of N, O, or S; X is a nullity, oxygen, sulfur, or nitrogen; $R_2'$ is a nullity or $C_1$-$C_{20}$ alkyl, $C_4$-$C_{20}$ ether; $C_1$-$C_{20}$ alkyl having a substituent of N, O, or S; $C_1$-$C_{20}$ ester; $C_1$-$C_{20}$ alcohol; $C_1$-$C_{20}$ alkenyl; heteroatom $C_6$-$C_{20}$ aryl, $C_6$-$C_{20}$ heterocyclic containing a heteroatom of N, O or S; Y is a carbon, nitrogen, oxygen, or sulfur nucleophilic group; and n is an integer between 1 and 30. $B^3$ is

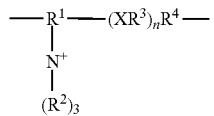

where $R^1$ is a $C_1$-$C_{20}$ alkyl; $C_4$-$C_{20}$ ether; $C_1$-$C_{20}$ alkyl having a substituent of N, O, or S; heteroatom $C_6$-$C_{20}$ aryl, $C_1$-$C_{20}$ carbonyl, $C_1$-$C_{20}$ amidyl, $C_1$-$C_{20}$ ether, $C_6$-$C_{20}$ aryl, $C_6$-$C_{20}$ heterocyclic containing a heteroatom of N, O, or S; $R^2$ is independently in each occurrence a H, a $C_1$-$C_{20}$ alkyl, a $C_2$-$C_{20}$ alkyl having a substituent of $C_1$-$C_{20}$ alkyl; X is independently in each occurrence a nullity, oxygen, sulfur, or nitrogen; $R^3$ is independently in each occurrence a nullity, $C_1$-$C_{20}$ alkyl, $C_1$-$C_{20}$ having a substituted $C_6$-$C_{20}$ aryl, $C_6$-$C_{20}$ heterocyclic containing a heteroatom of N, O or S; n is an integer between 0 and 30, inclusive; $R^4$ is independently in each occurrence a nullity, $C_1$-$C_{20}$ alkyl, $C_1$-$C_{20}$ having a substituted $C_6$-$C_{20}$ aryl, $C_1$-$C_{20}$ carbonyl, $C_1$-$C_{20}$ amidyl, $C_1$-$C_{20}$ ether, $C_6$-$C_{20}$ aryl, $C_6$-$C_{20}$ heterocyclic containing a heteroatom of N, O, or S; and $B^4$ is a nullity or $C_1$-$C_{20}$ alkyl, $C_4$-$C_{20}$ ether; $C_1$-$C_{20}$ alkyl having a substituent of N, O, or S; $C_1$-$C_{20}$ ester; $C_1$-$C_{20}$ alcohol; $C_1$-$C_{20}$ alkenyl; heteroatom $C_6$-$C_{20}$ aryl, $C_6$-$C_{20}$ heterocyclic containing a heteroatom of N, O or S.

In an alternative embodiment the inventive substrates A-$B^1$-$B^2$-$B^3$-$B^4$ are optionally synthesized with a non-hydrolyzable link between A and $B^1$. This produces suicide substrates that maintain high specificity for their target lysosomal enzyme whereby specificity is conferred by both the A and $B^4$ moieties. These molecules serve as more specific and potent inhibitors of enzyme function.

FIG. 1 shows α-D-glucose, modified with a 4-aminophenyl group is reacted with a differentially protected lysine group. Methods for differentially protecting lysine are known in the art and illustrative examples are described in WO 01/27074. The intermediate A-$B^1$-$B^2$ is formed which is specifically deprotected at the alpha-amino group to provide a suitable reactive site for subsequent synthetic steps. Methods of site-specific deprotection are known in the art. The alkyl chain is then added. An exemplary alkyl chain is provided by dodecyl-carnitine ($B^3$-$B^4$) which is synthetically added to the A-$B^1$-$B^2$ intermediate to form a full length substrate molecule (A-$B^1$-$B^2$-$B^3$-$B^4$). This substrate molecule is active as a GAA specific substrate and is optionally used in analyses involving mass spectrometry or other suitable assay and detection method. In another preferred embodiment, the 6-amino group on $B^2$ is deprotected so as to produce a similarly reactive substrate. It is appreciated in the art that synthesis of numerous derivatives of the above illustrated substrate are similarly achieved such as by varying the carbon chain on the acylcarnitine, altering the sugar A group or the $B^1$ group. Also, numerous derivatives of lysine ($B^2$) or other alkyl groups are similarly suitable.

It is appreciated in the art that similar synthetic pathways are suitable for production of the inventive substrates. FIG. 2 depicts a synthetic pathway similar to FIG. 1 except for the protective groups and the choice of acylcarnitine whereby n is a value between 1 and 30. Preferably, n is between 1 and 20.

FIG. 3 depicts an exemplary substrate structure for detecting lysosomal storage diseases. The structure is composed of a sugar (A) in the form of a glucose or a galactose and an aliphatic group B. Group B is further composed of a linker arm ($B^1$) in the form of a nitrophenyl, a $B^2$ subgroup of a lysine, a $B^3$ subgroup of a carnitinyl, and a $B^4$ subgroup in the form of an alkyl with carbon length in the range of 10 to 30. A quaternary ammonium cation located on the $B^3$ subgroup avoids the need of further ionization otherwise needed for mass spectrometry detection.

FIG. 4 depicts the multiple functional groups that provide multiple assay format detection of enzymatic activity. The terminal amino group on $B^2$ is capable of forming covalent bonds with carboxylic acids on solid supports. The presence of the quaternary ammonium on $B^3$ provides a permanently charged moiety such that subsequent ionization is not required for analysis by MS/MS providing a robust and easily detectable and quantifiable detection of lysosomal enzyme activity.

FIG. 5 demonstrates a generic enzymatic reaction using an inventive substrate. Upon specific affinity binding and enzymatic reaction, the substrate is cleaved into two groups, a sugar moiety A and an aliphatic group B. The group B is optionally composed of a nitrophenyl, a lysine, a carnitinyl, and long-chain alkyl moieties. Both groups are optionally then analyzed by MS/MS. An internal standard is also concurrently subject to the MS/MS analysis. The internal standard is an isotopically labeled analog of B with deuterium to replace hydrogen atom(s) on a methyl group. Alternatively, the deprotected terminal amino group on $B^2$ is reactive with a solid support such that the presence or absence of product is optionally detected using immunoassay methods. The deprotected terminal amine can also be derivatized with a fluorescent reagent for HPLC, or other suitable detection method.

FIG. 6 illustrates exemplary inventive methods depicting detection of enzymatic reactions using mass spectrometry that are advantageous in comparison to prior art methods. The inventive method eliminates many steps inherent with the use of non-polar substrates and their relative internal standards. More specifically, the inventive method no longer needs steps to clean up non-polar solvent and or detergents the involvement of which is detrimental to mass spectrometry machinery. These steps include: the extraction of enzymatic products into chloroform by a liquid-liquid extraction step, the removal of the detergents by a silica-gel separation step, and the step of solid-phase extraction (SPE) process. These extra steps of the prior art add statistical error. Since the inventive substrates in accordance with the current invention are more polar in contrast to the prior art, polar solvents illustratively including pure methanol or pure ethanol are operative herein.

All reagents including the substrates, enzymatic products, and internal standards can be optionally purified by reverse-phase HPLC and characterized by ESI-MS, either in an online HPLC-MS assay or offline by collection of the appropriate fractions.

EXAMPLES

Example 1

For each sample, a disk of 3 mm diameter is punched from the areas of dried blood on a filter paper into a well of a 96-well microtiter plate. The blood disk is then incubated directly with an assay solution containing substrates directed to the Fabry disease at a final concentration of 5 mmol/L and internal standards at a final concentration of 0.1 mmol/L. To the assay solution, a final concentration of 0.5 mol/L sodium acetate buffer is also added. The assay mixture containing the blood disk is incubated for 15 to 24 hours at 37° Celsius with orbital shaking (150 rpm) in a thermostatic air shaker. After the incubation period, an aliquot of pure methanol is added to each tube or well to terminate the enzymatic reaction. Before going into the mass spectrometer, the incubated reaction mixture is diluted with pure methanol. For the mass spectrometry analysis, the electrospray source is operated in positive mode, and the ions are detected in parent-ion scan mode. The amount of enzymatic product is calculated from the ion abundance ratio of the product to the internal standard minus that of a blank.

Example 2

In an alternative embodiment the product of the reaction with the inventive substrates is quantified by immunoassay. Blood spotted on filter paper is reconstituted in buffer to liberate the active components. One or an array of inventive substrates are added to the reaction chamber and the reaction allowed to proceed overnight (~14 hours). The reaction is quenched by the addition of 6× volume glycine/NaOH pH 10.4. A sample of each reaction is added to the wells of a high-binding irradiated microtiter plate and incubated overnight to allow sufficient binding of the reaction product to the wells of the plate. A standard curve of product in similar buffer/sample is also added to the plate to serve as a basis for quantitation. After complete binding to the surface of the plate, the wells are washed twice with phosphate buffered saline (PBS) by the use of a squirt bottle, plate washer, or any other automated or non-automated plate washing system. Any additional sites for protein binding are subsequently blocked by the addition of a blocking agent illustratively including 3% bovine serum albumin in PBS or any other synthetic or natural blocking agent known in the art. The blocking agent is incubated for two hours at room temperature. The wells are washed 3× with PBS. The primary antibody(s) is then added to the wells to recognize and bind the remaining substrate, or the product. The antibody(s) is incubated in the wells for at least 2 hours. The plate is washed four times to remove unbound antibody. If the primary antibody is labeled the plate is used for detection. Optionally, a labeled secondary antibody is placed in the plate wells and allowed to incubate for an additional 2 hours followed by washing 4 times and detection by the appropriate method such as by a fluorescent or optical plate reader.

Example 3

In an alternative embodiment the product of the reaction with the inventive substrates is quantified by immunoassay. Blood spotted on filter paper is reconstituted in buffer to liberate the active components. One or an array of inventive substrates immobilized to encoded particles are added to the reaction chamber, preferably a microplate well, and the reaction allowed to proceed overnight (~14 hours). A standard curve of enzyme in similar buffer/sample is also added to separate sets of encoded particles to serve as a basis for quantitation. The reaction is quenched by the addition of 6× volume glycine/NaOH pH 10.4. The primary antibody(s) is then added to the wells to recognize and bind the remaining substrate, or the product. The antibody(s) is incubated for at least 30 minutes. If the primary antibody is labeled the assay is ready for detection. Optionally, a labeled secondary antibody is placed in the plate wells and allowed to incubate for an additional 30 minutes. Detection is accomplished a flow cytometer.

Example 4

The active amino group on the $B^2$ of a preferred embodiment is amenable to numerous labeling procedures. Among these, fluorescent labeling offers one of the most powerful methods of detection as it provides excellent sensitivity, ability to quantitate relative to a standard, and can be combined with other substrates with other fluorophores in a panel assay for multiple lysosomal enzymes. In a representative example, the $B^2$ side chain amine is specifically labeled with fluoroisothiocyanate (FITC). Derivitization of the inventive substrate of FIG. 1 is performed by addition of a FICT molecule to the terminal amine of the $B^2$ group. The purified/lyophilized substrate is resuspended in 0.1 M sodium bicarbonate buffer, pH 9.0 at a concentration of 5 mg/ml. Immediately prior to reaction with substrate, dissolve 5 mg of FITC dye in 0.5 ml of DMSO in the dark. With gentle vortexing, add 0.1 ml of dye solution of the substrate solution and incubate for 1 hour at room temperature in the dark. The free unreacted dye is removed by gel filtration on a 10×300 mm Sephadex G column pre-equilibrated in phosphate buffered saline. Concentration of the final product is determined by mass spectrometry or other method known in the art. The labeled substrate is optionally concentrated and aliquoted for storage at −20° C. until further use.

The labeled substrate is used in a reaction for the detection of glucocerebrosidase activity and the detection of Gaucher's disease. For each patient or control sample, a disk of 3 mm diameter is punched from the areas of dried blood on a filter paper into a micro-centrifuge tube or a well of a 96-well microtiter plate. The blood disk is then incubated directly with an assay solution containing labeled inventive substrate at a final concentration of 5 μmol/L and internal standards at a final concentration of 0.1 mmol/L. The assay mixture containing the blood disk is incubated for 15 to 24 hours at 37° C. with orbital shaking (150 rpm) in a thermostatic air shaker. After the incubation period, an aliquot of pure methanol is added to each tube or well to terminate the enzymatic reaction. A sample of the reaction is added to a second tube containing a HPLC mobile phase (methanol:water:acetic acid, 82:18:0.1 vol/vol/vol). A 20-μl aliquot of the quenched reaction solution is separated on a 4.6×250-mm Symmetry $C_{18}$ reverse-phase HPLC column (Waters, Milford, Mass.) isocratically, at a rate of 1.3 ml/min using methanol:water: acetic acid at 82:18:0.1 vol/vol/vol as a mobile phase. Fluorescence intensity is continuously monitored using a fluorescence detector (model L-7480; Hitachi, Naperville, Ill.) at a medium gain sensitivity. The amount of labeled product in the sample is determined by comparing the area of the peak to that of an external standard comprised of labeled product at a known concentration. The concentration of product in the reaction is readily determined and the activity of glucocerebrosidase determined by dividing the moles product/per unit of reaction time.

Example 5

In an alternative embodiment the product of the reaction with the inventive substrates is quantified by immunoassay wherein a specific antibody targeted to the cleaved inventive substrate is employed. Blood spotted on filter paper is resolubilized in buffer to liberate the active components. One or an array of inventive substrates are added to the reaction chamber and the reaction allowed to proceed overnight (~14 hours). The reaction is quenched by the addition of 6× volume glycine/NaOH pH 10.4. A microtiter plate is prepared in advance by coating with an antibody generated in a mouse that is specific for the nitrophenyl-aminoacyl $B^1$-$B^2$ moiety. Any additional sites for protein binding are subsequently blocked by the addition of a blocking agent illustratively including 3% bovine serum albumin in PBS or any other synthetic or natural blocking agent known in the art. A sample of each reaction is added to the wells of a microtiter plate and incubated for two hours to overnight to allow sufficient binding of the reaction product to the wells of the plate. A standard curve of control product in similar buffer/sample is also added to the plate to serve as a basis for quantitation. After complete binding to the surface of the plate, the wells are washed twice with phosphate buffered saline (PBS) by the use of a squirt bottle, plate washer, or any other automated or non-automated plate washing system. The primary antibody(s) is then added to the wells to recognize and bind the product at an alternative epitope. The antibody(s) is incubated in the wells for at least 2 hours. The plate is washed four times to remove unbound antibody. If the primary antibody is labeled the plate is used for detection. Optionally, a labeled secondary antibody is placed in the plate wells and allowed to incubate for an additional 2 hours followed by washing 4 times and detection by the appropriate method such as by a fluorescent or optical plate reader.

Any patents or publications mentioned in this specification are indicative of the levels of those skilled in the art to which the invention pertains. These patents and publications are herein incorporated by reference to the same extent as if each individual publication was specifically and individually indicated to be completely incorporated by reference.

One skilled in the art will readily appreciate that the present invention is well-adapted to carry out the objects and obtain the ends and advantages mentioned, as well as those inherent therein. The present examples along with the methods, procedures, treatments, molecules and specific compounds described herein are presently representative of preferred embodiments, are exemplary, and are not intended as limitations on the scope of the invention. It will be apparent that other embodiments exist and are encompassed within the spirit of the invention as defined by the scope of the claims.

The invention claimed is:

1. A molecule comprising the formula:

$$B^1\text{-}B^2\text{-}B^3\text{-}B^4 \qquad (I)$$

where $B^1$ is a methylene or 4-aminophenol; $B^2$ is a diaminohexanoyl or an amidylaminoacyl said $B^2$ covalently bound to $B^1$ by an amide bond and to $B^3$ by an amide bond;

$B^3$ includes a quaternary ammonium and is a carnitinyl;

and $B^4$ is an alkyl chain with 10-20 carbons linked to $B^3$ via an ester bond.

2. The molecule of claim 1 wherein $B^1$ is a 4-aminophenol.

3. The molecule of claim 1 where $B^2$ is a lysine.

4. The molecule of claim 1 wherein $B^2$ is derivatized by the addition of a fluorophore.

5. The molecule of claim 1 wherein ($B^1$-$B^2$-$B^3$-$B^4$) includes a stable secondary prevalence isotope of an element.

6. The molecule of claim 5 wherein said stable secondary prevalence isotope in each occurrence is selected from the group consisting of $^2D$, $^{13}C$, $^{15}N$, $^{17}O$, $^{18}O$, $^{31}P$ and $^{34}S$.

7. A method for detecting enzymatic activity, comprising: contacting a sample containing a target enzyme with a substrate having the formula:

$$A\text{-}B^1\text{-}B^2\text{-}B^3\text{-}B^4$$

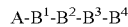

where A is a monosaccharide or a disaccharide, said A covalently bound to said $B^1$, and wherein said $B^1$-$B^2$-$B^3$-$B^4$ is the molecule of claim 1, under conditions wherein the target enzyme is capable of acting on the substrate to produce an enzymatic product; and detecting the amount of the enzymatic product.

8. The method of claim 7 wherein the $B^2$ of said enzymatic product is derivatized by the addition of a fluorophore.

9. The method of claim 7 wherein said substrate is linked to a solid support.

10. The method of claim 7 wherein said detecting is by detecting the amount of substrate remaining on the solid support.

11. The method of claim 7 wherein said $B^1$-$B^2$-$B^3$-$B^4$ includes a stable secondary prevalence isotope of an element.

12. The method of claim 11 wherein said stable secondary prevalence isotope in each occurrence is selected from the group consisting of $^2D$, $^{13}C$, $^{15}N$, $^{17}O$, $^{18}O$, $^{31}P$ and $^{34}S$.

* * * * *